United States Patent [19]

Shah

[11] 4,337,325
[45] Jun. 29, 1982

[54] PRESSURE-SENSITIVE ADHESIVE

[75] Inventor: Kishore R. Shah, Chelmsford, Mass.

[73] Assignee: The Kendall Company, Boston, Mass.

[21] Appl. No.: 137,297

[22] Filed: Apr. 4, 1980

Related U.S. Application Data

[63] Continuation-in-part of Ser. No. 956,061, Oct. 30, 1978, abandoned.

[51] Int. Cl.$^3$ .................... C08L 35/00; C08L 39/06
[52] U.S. Cl. .................... 525/205; 428/355
[58] Field of Search ........................ 525/205

[56] References Cited

U.S. PATENT DOCUMENTS 3,027,347  3/1962  Kentscher et al. ............... 525/205
3,928,262  12/1975  Ono et al. ....................... 525/205

Primary Examiner—J. Ziegler

[57] ABSTRACT

An optically clear blend of (1) a water-soluble polymer of a vinyl lactam having the structure

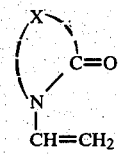

in which X represents an alkylene bridge having three to five carbon atoms or a copolymer thereof with 1 to 80 mole percent of a copolymerizable monomer containing a polymerizable ethylenic unsaturation; and (2) a tacky water-insoluble copolymer of (A) an ester or a mixture of esters having the structure

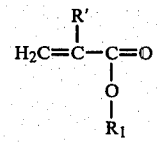

in which R' represents hydrogen or methyl and $R_1$ represents alkyl having from 1 to 14 carbon atoms and (B) from 1 to 12% by weight, based on the copolymer, of an ethylenic monomer containing an acid group, the vinyl lactam polymer or copolymer being present in an amount from 1 to 30% by weight of the blend and having a glass transition temperature from 20° to 150° C., and the tacky copolymer having a glass transition temperature below 0° C. and being present in an amount from 70 to 99% by weight of the blend and having a viscosity less than 50,000 cp at 350° F. The blend is useful as a pressure-sensitive adhesive composition.

8 Claims, No Drawings

PRESSURE-SENSITIVE ADHESIVE

This application is a continuation-in-part of my co-pending application Ser. No. 956,061 filed Oct. 30, 1978, now abandoned.

This invention relates to a composition useful as a pressure-sensitive adhesive which is a blend of a poly(vinyl lactam) or of a copolymer of a vinyl lactam with 1 to 80 mole percent of copolymerizable monomer containing a polymerizable ethylenic unsaturation, and an interpolymer of (1) an acrylic or methacrylic ester or a mixture of esters and (2) an ethylenically unsaturated acid, the blend possessing a unique combination of properties and characteristics.

Pressure-sensitive adhesive compositions are commonly applied to the flexible backing or tape on which they are supported during use by coating them in the form of a solution or dispersion in a suitable vehicle such as an organic solvent or water or by coating them in the form of a hot melt free from vehicle. In order to be useful, pressure-sensitive adhesive compositions must possess not only good tack but also good cohesive strength and the desired high degree of adhesion. All of these properties are generally interdependent, a change in one usually causing a change in the others. Although various low molecular weight homopolymers of alkyl acrylates have long been known to be tacky materials, they have possessed insufficient cohesive strength to be useful by themselves as pressure-sensitive adhesives, particularly those of the type used on tapes or backings intended to adhere to the skin, and it has been necessary to copolymerize them with selected other monomers to achieve the desired combination of properties, as described for example in Samour U.S. Pat. No. 3,299,010.

It has also long been the practice to formulate pressure-sensitive adhesive compositions by blending together compatible components each of which in itself lacks one or more of the required properties but which combine to satisfy the requirements, as in the case of blends of two different hydrophobic water-insoluble copolymers as described in Guerin et al. U.S. Pat. No. 4,045,517. It has also been proposed to react water-soluble poly(N-vinyl lactams) with polymeric carboxylic acids (including copolymers) to form water-insoluble compositions useful for a variety of purposes, as described in Stoner et al. U.S. Pat. No. 2,901,457. As pointed out by Stoner et al. at column 4, lines 56-73, the reaction product there described always has substantially the same properties and contains the two polymeric components in the same proportions regardless of the proportions of the two used to make the product. The compositions of the present invention, on the other hand, vary in properties and in proportions of components depending upon proportions of starting materials. Moreover, it has been reported in Boyer-Kawenoki, Compt. Rend., Ser. C, Vol. 263, p. 278 (Chem. Abs. Vol. 65, 20283d) 1966 that an I.R. spectrum of the addition product of poly(vinyl pyrrolidone) and poly(acrylic acid) indicated hydrogen bonding between the pyrrolidone carbonyl groups and the carboxyl groups of the poly(acrylic acid). In Ono et al. U.S. Pat. No. 3,975,570, it has been proposed to improve the moisture permeability of conventional pressure-sensitive adhesives which are copolymers of alkyl acrylates with acrylic or methacrylic acid by blending with them hydroxyethyl cellulose, and it was stated that blends of such adhesives with poly(vinyl pyrrolidone) did not exhibit improved moisture permeability. Other blends of a poly(vinyl lactam) with various copolymers are described and claimed in copending applications of Shah Ser. No. 957,885 filed Nov. 6, 1978, now abandoned, Shah Ser. No. 100,375 filed Dec. 5, 1979, now abandoned, and Shah Ser. No. 201,349, filed Oct. 27, 1980, now U.S. Pat. No. 4,300,820; and of Shah and Temin Ser. No. 963,898 filed Nov. 27, 1978, now abandoned.

It has now been found that water-insoluble pressure-sensitive adhesive compositions having excellent tack, cohesion, and adhesion and capable of being applied to a backing by conventional hot melt coating equipment can be made by preparing an optically clear blend comprising (1) a water-soluble polymer of certain N-vinyl lactams or a copolymer thereof with 1 to 80 mole percent of a copolymerizable monomer containing a polymerizable ethylenic unsaturation, and (2) a water-insoluble tacky copolymer of an (A) an ester or a mixture of esters having the structure

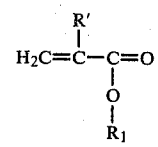

in which R' represents hydrogen or methyl and $R_1$ represents alkyl having 1 to 14 carbon atoms and (B) from 1 to 12%, preferably from 4 to 7% by weight of the copolymer of an ethylenic monomer containing an acid group, the vinyl lactam polymer or copolymer having a glass transition temperature from 20° to 150° C., and the tacky copolymer having a glass transition temperature below 0° C., and having a viscosity of less than 50,000 cp at 350° F., and being soluble in organic solvents (i.e., substantially free from cross-linking), so that it possesses by itself insufficient cohesive strength to be useful as a pressure-sensitive adhesive.

The N-vinyl lactams, polymers and copolymers of which can be used in the present invention include those having the structure

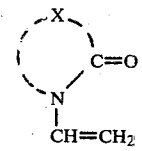

in which X represents an alkylene bridge having three to five carbon atoms, such as 1-vinyl-2-pyrrolidone, 1-vinyl-5-methyl-2-pyrrolidone, 1-vinyl-2-piperidone, and N-vinyl-ε-caprolactam. The copolymerizable monomers with which the N-vinyl lactams can be copolymerized to form copolymers containing 20 to 99 mole percent N-vinyl lactam and correspondingly 1 to 80 mole percent of comonomer, include vinyl acetate and alkyl acrylates and methacrylates in which the alkyl group contains from 1 to 14 carbon atoms. These polymers and copolymers may have molecular weights from 10,000 to 1,000,000 or more, and they have a glass transition temperature from 20° to 150° C. The copolymer may or may not be water soluble. Polymers and copolymers of 1-vinyl-2-pyrrolidone are preferred. The amount of N-vinyl lactam polymer or copolymer in the blend can vary from 1 to 30% by weight of the blend, depending upon the precise polymer or copolymers present and the precise properties desired in the blend.

The amount of tacky copolymer present in the blend can be varied from 70 to 99% by weight of the blend. Preferably, the pressure-sensitive adhesive composition contains only the blend of polymeric or copolymeric N-vinyl lactam and the specified tacky copolymer, although small amounts of conventional additives such as stabilizing agents, may also be present to prevent deterioration of the blend during processing at elevated temperatures. Other conventional additives such as pigments, coloring agents, etc. may also be present.

The ethylenic monomer containing an acid group which is copolymerizable with the ester to form the tacky copolymer can contain a carboxylic acid group or sulfonic or phosphonic, such as acrylic or methacrylic acid, crotonic acid, maleic acid, 2-sulfoethyl methacrylate, and 1-phenyl vinyl phosphonic acid. Preferably the acid group in the ethylenic monomer is carboxylic, acrylic acid being the monomer of choice. The ester with which the ethylenically unsaturated monomeric acid is copolymerized to form the tacky copolymer may be for example butyl acrylate, 2-ethylhexyl acrylate, lauryl acrylate and the corresponding methacrylates or mixtures thereof. Esters of acrylic acid with mixtures of different alcohols having from 1 to 14 carbon atoms are preferred; particularly preferred are alkyl acrylates in which the alkyl groups have from 4 to 8 carbon atoms. The copolymer need not be one consisting solely of the specified ester monomer and ethylenic monomer containing an acid group but may contain up to 20%, by weight of the total copolymer, of another copolymerizable ethylenically unsaturated monomer such as vinyl acetate, styrene, acrylonitrile, etc. In general, the presence of such a third comonomer in the copolymer does not adversely affect the properties of the pressure-sensitive adhesive and may be desirable in some cases to reduce cost or to increase cohesive strength.

The blend can be made by mixing together solutions or dispersions of the N-vinyl lactam polymer or copolymer and of the tacky copolymer in any desired vehicles or solvents which are miscible with each other, then removing the vehicle or solvent, as by evaporation. It is also possible to blend the polymers or copolymers on conventional mixing equipment such as a two-roll mill or Sigma blade mixer. Indeed, the blend can be formed by stirring into a solution of the N-vinyl lactam polymer or copolymer, for example, the solution resulting from the polymerization reaction itself in the case of a copolymer, the desired monomers in the desired proportions for the tacky copolymer, adding an initiator, and heating to form the tacky copolymer in the same solution. The solvent can be removed by volatilization after completion of the second polymerization.

In the case of those blends containing amounts of N-vinyl lactam polymer or copolymer near the upper end of the specified range of proportions, i.e., from 10-30% by weight of the blend, the pressure-sensitive adhesive composition displays increased moisture vapor permeability as compared to compositions containing smaller amounts of the polymer. This is an advantageous feature in the case of adhesive tapes or sheets having porous backing or reinforcement which are intended to be applied to the skin.

Although different polymers and copolymers are normally considered to be incompatible with one another when mixed, and incapable of forming a homogeneous blend having properties different from either of the components, the blends of the present invention are optically clear or at worst slightly hazy in appearance, evidence that the blends are homogeneous at least to the extent that no discrete particles of either component greater than 4000 Å in diameter are present. Because of this homogeneity, the low cohesive strength of the tacky copolymer is increased and the high fluidity is decreased by the presence in the blend of the N-vinyl lactam polymer or copolymer which acts as a reinforcing agent.

The blends of the present invention can be applied to any of the usual flexible backings or reinforcements employed in manufacturing adhesive tapes and sheets either by spreading, coating or casting a mixed solution or dispersion of the blend on the backing, then removing solvent or liquid vehicle, for example by evaporation; however, the blends possess the unique capability of being applied in molten condition using conventional hot melt coating equipment because their hot melt viscosities are less than 100,000 cps at 350° F.; no curing or cross-linking of the blend is required. Conventional pressure-sensitive adhesives containing copolymers of alkyl acrylates and acrylic or methacrylic acid of sufficiently high viscosity to have adequate cohesive strength, have a melt viscosity above 100,000 cps at 350° F. and cannot be applied to a backing in molten condition using conventional equipment.

In order to achieve maximum stability and service life of the blend, it may be desirable to include in the pressure-sensitive adhesive composition, in addition to the N-vinyl lactam polymer or copolymer and the tacky copolymer, a small amount of conventional stabilizer such as 1% by weight of tetrakis-[2,4-ditert-butylphenyl]-4,4'-biphenylylenediphosphonite.

The following specific examples are intended to illustrate more fully the nature of the present invention without acting as a limitation upon its scope. The molecular weights referred to herein are the peak molecular weights as determined by gel permeation chromatography.

EXAMPLES 1-15

A series of tacky copolymers of alkyl acrylates with varying proportions of acrylic acid was prepared by conventional solution polymerization procedures by dissolving the desired proportions of monomers in a suitable solvent such as benzene or ethyl acetate and by employing as the initiator of polymerization a small amount (0.1% by weight of the monomers) of a free radical generator such as benzoyl peroxide or 2-t-butylazo-2-cyanopropane. Polymerization was carried out at 85°-95° C. to a high degree of conversion, of the order of 97%, to provide copolymers having insufficient cohesive strength to be useful by themselves as pressure sensitive adhesives having molecular weights from 62,000 to 566,000. These copolymers after removal of the solvent by heating in vacuum were aggressively tacky in nature but lacked sufficient cohesive strength to be satisfactory pressure-sensitive adhesives by themselves. A tabulation of the copolymers and of their molecular weights follows:

| No. | Acrylic Ester | Wt. Ratio of Acrylic Ester to Acid | Mol. Wt., Thousands |
|---|---|---|---|
| (1) | n-Butyl | 98:2 | 82 |
| (2) | n-Butyl | 97:3 | 127 |

-continued

| No. | Acrylic Ester | Wt. Ratio of Acrylic Ester to Acid | Mol. Wt., Thousands |
|---|---|---|---|
| (3) | n-Butyl | 97:3 | 200 |
| (4) | n-Butyl | 95:5 | 58 |
| (5) | 2-Ethylhexyl | 98:2 | 566 |
| (6) | 2-Ethylhexyl | 97:3 | 128 |
| (7) | 2-Ethylhexyl | 97:3 | 207 |
| (8) | 2-Ethylhexyl | 96.5:3.5 | 304 |
| (9) | 2-Ethylhexyl | 96:4 | 62 |
| (10) | 2-Ethylhexyl | 96:4 | 84 |
| (11) | 2-Ethylhexyl | 96:4 | 112 |
| (12) | 2-Ethylhexyl | 95.3:4.7 | 105 |
| (13) | 2-Ethylhexyl | 94.5:5.5 | 85 |
| (14) | 2-Ethylhexyl | 94.5:5.5 | 105 |
| (15) | 2-Ethylhexyl | 93:7 | 105 |
| (16) | 2-Ethylhexyl | 96:4 | — |
| (17) | 2-Ethylhexyl | 92:8 | — |
| (18) | n-Butyl | 96:4 | — |

A series of 1-vinyl-2-pyrrolidone homopolymers, all water-soluble but having differing reported molecular weights, was obtained from commercial sources, as follows:

| No. | Polyvinyl Pyrrolidone Mol.Wt., Thousands |
|---|---|
| (1) | 10 |
| (2) | 40 |
| (3) | 360 |

In addition, a series of 1-vinyl-2-pyrrolidone copolymers containing varying proportions of vinyl acetate, butyl methacrylate and methyl methacrylate was prepared by dissolving the desired proportions of monomers in a suitable solvent such as ethyl acetate, or a mixture of dioxane and ethyl alcohol, etc. and by employing as initiator approximately 0.1% by weight of a free radical generator such as benzoyl peroxide or azo bis-isobutyronitrile. Polymerization was carried out at 85°–95° C. to a degree of conversion of about 90%, and the copolymer was precipitated in purified form by pouring a dilute solution (ca. 10% by weight) drop by drop into an excess of methanol. These copolymers had the following compositions:

| No. | Comonomer | Mol. Ratio of Comonomer: 2-vinyl pyrrolidone |
|---|---|---|
| (4) | Butyl Methacrylate | 75:25 |
| (5) | Butyl Methacrylate | 80:20 |
| (6) | Butyl Methacrylate | 68:32 |
| (7) | Methyl Methacrylate | 75:25 |
| (8) | Methyl Methacrylate | 70:30 |
| (9) | Vinyl Acetate | 75:25 |

Blends of the foregoing two series in varying proportions by weight were then prepared as shown in Table I. In some cases, the tacky acrylate copolymer, still in solution in the solvent in which it was polymerized, was mixed with a solution of the poly(vinyl pyrrolidone) in a compatible solvent such as chloroform and the two solvents were then removed by volatilization at reduced pressure. In other cases, the solvent was first removed from the solution of tacky acrylate copolymer by heating at reduced pressure and the solvent-free copolymer was then blended with solvent free poly(vinyl pyrrolidone) by milling on a heated 2-roll mill. The blend was then applied to a standard backing or support consisting of a 1.5 ml polyethylene terephthalate film (Mylar), the blends which were formed in solution being applied by spreading the solution on the film before evaporating the solvent and the blends formed by milling being applied by calendering. The product in each case was a pressure-sensitive adhesive tape having an adhesive layer from 1–3 mils in thickness.

The adhesive properties of the tape were then determined with the results set forth in the following table. The probe tack was determined by means of a Polyken probe tack tester as described in U.S. Pat. No. 3,214,971 having the following four functional parts: (1) a cylindrical steel probe attached to the compression loaded spring of (2) a series L Hunter mechanical force gauge (Hunter Spring Company, Brochure 750/FG, revised Feb. 1961), (3) an annulus having an opening slightly larger than the diameter of the probe and (4) a carrier for the annulus which moves down to bring the annulus around the probe and then up to remove the annulus therefrom. The carrier moves at a speed of 0.1 inch per second. At the beginning of the test, the carrier is at its uppermost point of travel and the annulus rests upon the carrier so that the opening in the annulus is in line with the probe positioned beneath it. In carrying out the test, a strip of tape is placed upon the annulus, adhesive side down, and spanning the annulus, opening. As the carrier is driven downwardly by the synchronous motor, the adhesive surface exposed through the opening is brought into contact with the flat surface of the probe so that the tape and the annulus attached thereto are suspended on the probe as the carrier continues farther on its downward path. The carrier then reverses its movement returning to pick up the annulus, thereby separating the tape from the probe surface. Separation begins after one second contact between the probe and the adhesive. The force required to separate the tape from the probe is recorded on a gauge. The recorded value is the probe tack value. Measurements were made employing a loading of 100 grams/cm.$^2$.

The peel adhesion values represent the forces required to remove a one-inch wide adhesive tape from a stainless steel surface after contact therewith for 2 minutes at a temperature of about 75° F. The tape is stripped from the surface at an angle of 180° at a rate of 12 inches per minute.

The creep resistance values are determined by providing a polished stainless steel tube, one inch in outside diameter, mounted horizontally within a constant temperature chamber maintained at 104° F.±2° F. The tube is provided with a slot 1/16 inch wide extending along its upper face parallel to the tube axis. A six inch length of adhesive tape to be tested is draped over the tube with its adhesive surface in contact with the tube and with its free ends extending downwardly approximately the same distance on opposite sides of the tube, the tape extending across the slot perpendicularly thereto. Each length of tape is not over one-inch wide and to each of its lower ends is secured a weight of one pound per inch of tape width. After the weighted tape has been maintained in the chamber for 15 minutes, it is severed transversely along the gap in the slot and the time in hours required for downward movement of each end by a distance of one-half inch is measured. The creep resistance is expressed in hours.

The melt viscosity at 350° F. is measured as Brookfield Thermosel (Viscometer Model RVT) viscosity using a No. SC4-27 spindle at 2.5 rpm.

The results are as follows:

TABLE I

| Acrylic Copolymer No. | Vinyl Pyrrolidone Polymer or Copolymer No. | Wt. Ratio Copolymer:PVP | Viscosity at 350° F. cps × $10^{-3}$ | Probe Tack at 100g/cm$^2$ | Adhesion to Steel oz/in.width | Creep in hour Round Bar at 100° F., hours |
|---|---|---|---|---|---|---|
| 1 | 3 | 90:10 | <100 | 404 | 5.0 | 100+ |
| 1 | 2 | 90:10 | <100 | 930 | 48.0 | 0.3 |
| 3 | 2 | 87:13 | <100 | 228 | 43.0 | 100+ |
| 4 | 2 | 93:7 | <100 | 336 | 44.5 | 1.1 |
| 4 | 2 | 90:10 | <100 | 166 | 33.5 | 1.3 |
| 5 | 2 | 95:5 | <100 | 398 | 40 | 10.0 |
| 5 | 1 | 90:10 | <100 | 300 | 33 | 100+ |
| 5 | 2 | 90:10 | <100 | 262 | 31.5 | 100+ |
| 5 | 3 | 90:10 | <100 | 238 | 18.0 | 100+ |
| 7 | 2 | 90:10 | <100 | 140 | — | 100+ |
| 7 | 2 | 85:15 | <100 | 152 | — | 100+ |
| 8 | 2 | 90:10 | <100 | 308 | — | 100+ |
| 8 | 2 | 85:15 | <100 | 216 | — | 100+ |
| 9 | 1 | 94:6 | 4 | 944 | 47 | 0.2 |
| 9 | 2 | 94:6 | 6.3 | 260 | 53 | 7.0 |
| 9 | 2 | 92:8 | 15.0 | 250 | 35 | 11.4 |
| 9 | 3 | 98:2 | 25.0 | 518 | 28 | 2.6 |
| 10 | 1 | 94:6 | 7.0 | 972 | 74 | 0.2 |
| 10 | 2 | 96:4 | 15.0 | 332 | 27 | 4.2 |
| 10 | 3 | 98:2 | 58.0 | 684 | 46 | 3.8 |
| 11 | 1 | 94:6 | 24.0 | 460 | 50 | 11.2 |
| 11 | 2 | 96:4 | 38.0 | 262 | 26 | 16.6 |
| 12 | 2 | 96:4 | 44.0 | 218 | 21 | 40.0 |
| 13 | 2 | 96:4 | 22.0 | 296 | 30 | 22.0 |
| 14 | 2 | 96:4 | 60.0 | 190 | 23 | 100+ |
| 15 | 2 | 96:4 | 98.0 | 144 | 18 | 100+ |
| 16 | 4 | 85:15 | 16.5 | 412 | 38 | 3.5 |
| 16 | 4 | 80:20 | 28.8 | 236 | 33 | 6.0 |
| 16 | 4 | 75:25 | 22.0 | 99 | 38 | 11.1 |
| 16 | 4 | 70:30 | 41.8 | 0 | 39 | 22.7 |
| 17 | 4 | 85:15 | 39.8 | 710 | 45 | 0.4 |
| 17 | 4 | 80:20 | 61.3 | 179 | 45 | 5.8 |
| 17 | 4 | 75:25 | 64.5 | 0 | 30 | 69.9 |
| 17 | 4 | 70:30 | 81.0 | 0 | 10 | >100 |
| 16 | 5 | 85:15 | 10.3 | 506 | 59 | 1.5 |
| 16 | 5 | 80:20 | 22.3 | 134 | 50 | 4.1 |
| 16 | 5 | 75:25 | 30.8 | 57 | 40 | 10.5 |
| 16 | 5 | 70:30 | 49.5 | 0 | 42 | 22.3 |
| 17 | 5 | 85:15 | 37.5 | 651 | 44 | 0.4 |
| 17 | 5 | 80:20 | 58.3 | 64 | 40 | 4.6 |
| 17 | 5 | 75:25 | 56.3 | 0 | 30 | 21.9 |
| 17 | 5 | 70:30 | — | 0 | 14 | 62.2 |
| 16 | 6 | 85:15 | — | 183 | 24 | 11.9 |
| 16 | 6 | 80:20 | — | 12 | 25 | 31.4 |
| 16 | 6 | 75:25 | — | 7 | 30 | 72.4 |
| 16 | 6 | 70:30 | — | 0 | 26 | 72.6 |
| 17 | 6 | 85:15 | — | 486 | 40 | 1.5 |
| 17 | 6 | 80:20 | — | 34 | 38 | >100 |
| 17 | 6 | 75:25 | — | 0 | 15 | >100 |
| 17 | 6 | 70:30 | — | 0 | 0.8 | >100 |
| 16 | 7 | 90:10 | — | 368 | 27 | 31.9 |
| 16 | 7 | 85:15 | — | 252 | 18 | 54.3 |
| 16 | 7 | 80:20 | — | 73 | 8 | >100 |
| 17 | 7 | 90:10 | — | 0 | 11 | >100 |
| 17 | 7 | 85:15 | — | 0 | 2 | >100 |
| 17 | 7 | 80:20 | — | 0 | 3 | >100 |
| 16 | 8 | 85:15 | — | 312 | 24 | 42.5 |
| 16 | 8 | 80:20 | — | 174 | 18 | >100 |
| 17 | 8 | 90:10 | — | 137 | 30 | >100 |
| 17 | 8 | 85:15 | — | 8 | 16 | >100 |
| 17 | 8 | 80:20 | — | 0 | 7 | >100 |
| 16 | 9 | 85:15 | — | — | 24 | — |
| 18 | 9 | 85:15 | — | — | 40 | — |
| 18 | 4 | 85:15 | — | — | 43 | — |

Certain compositions of blends of alkyl acrylate copolymers containing higher proportions of PVP possess two times or greater water permeability (Table II) than the conventional non-blended acrylate pressure sensitive adhesives. Water permeability of an adhesive is a desirable characteristic especially in health care adhesive tape products for application to skin. It is measured by ASTM E96 Procedure E.

TABLE II

| Acrylic Copolymer No. | Poly(vinyl pyrrolidone) No. | Wt. Ratio Copolymer:PVP | Probe Tack at 100g/cm$^2$ | Adhesion to Steel oz/in. width | Creep in hour Round Bar at 100° F., hours | Water Vapor Transmission Rate in gms of water/100IN$^2$/24 hrs |
|---|---|---|---|---|---|---|
| 3 | 2 | 87:13 | 252 | 26.6 | 7.9 | 110 |

TABLE II-continued

| Acrylic Copolymer No. | Poly(vinyl pyrrolidone) No. | Wt. Ratio Copolymer:PVP | Probe Tack at 100g/cm$^2$ | Adhesion to Steel oz/in. width | Creep in hour Round Bar at 100° F., hours | Water Vapor Transmission Rate in gms of water/100IN$^2$/24 hrs |
|---|---|---|---|---|---|---|
| 6 | 2 | 75:25 | 187 | 20.0 | 100+ | 91.0 |
| 6 | 3 | 75:25 | 143 | 16.7 | 100+ | 95.0 |

The blend in each of the examples is an optically clear mixture (the term includes very slightly hazy mixtures) and, as can be seen from the foregoing, all of the blends form useful pressure-sensitive adhesive tapes. It is also clear from the foregoing tabulation what effect is produced by variations in the amount of acrylic acid present in the tacky copolymer, the molecular weight of the copolymer, the relative proportion of copolymer to vinyl pyrrolidone polymer or copolymer, and the molecular weight of the poly(vinyl pyrrolidone). For optimum pressure sensitive adhesive properties of the blend, in general, smaller proportions of the N-vinyl lactam copolymer, and also smaller proportions of N-vinyl lactam in that copolymer, are required as the amount of acid comonomer in the tacky copolymer increases. The properties of other blends of the present invention can readily be determined by extrapolation or interpolation from the results set forth above, bearing in mind that in general, lesser amounts of acid comonomers are required, when a sulfonic or phosphonic acid group is present, to achieve the same effect as when a carboxylic acid group is used.

Similar results can be obtained using copolymers of acrylic acid with other alkyl acrylates or mixtures thereof and by using other water-soluble polyvinyl lactams in place of poly(vinyl pyrrolidone).

What is claimed is:

1. A composition consisting essentially of an optically clear blend of (1) a water-soluble polymer of a vinyl lactam having the structure

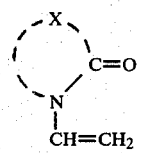

in which X represents an alkylene bridge having three to five carbon atoms, or a copolymer thereof with 1 to 80 mole percent of copolymerizable monomer containing a polymerizable ethylenic unsaturation, and (2) a tacky water-insoluble copolymer comprising (A) an ester or a mixture of esters having the structure

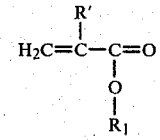

in which R' represents hydrogen or methyl and $R_1$ represents alkyl having from 1 to 14 carbon atoms and (B) from 1 to 12% by weight, based on the tacky copolymer of an ethylenic monomer containing an acid group, said vinyl lactam polymer or copolymer being present in an amount from 1 to 30% by weight of the blend and having a glass transition temperature from 20° to 150° C., and the tacky copolymer having a glass transition temperature below 0° C. and being present in an amount from 70 to 99% by weight of the blend and being substantially free from cross-linking and having a viscosity less than 50,000 cps at 350° F. so that it possesses by itself insufficient cohesive strength to be useful as a pressure-sensitive adhesive, said blend having a viscosity less than 100,000 cps at 350° F.

2. A composition as claimed in claim 1 in which X represents —CH$_2$—CH$_2$—CH$_2$—.

3. A composition as claimed in claim 2 in which R' represents hydrogen and (B) is acrylic acid.

4. A composition as claimed in claim 2 in which said vinyl lactam is present as a copolymer with vinyl acetate, an alkyl acrylate or an alkyl methacrylate.

5. A composition as claimed in claim 3 in which $R_1$ represents alkyl having from 4 to 8 carbon atoms.

6. A composition as claimed in claim 4 in which $R_1$ represents n-butyl.

7. A composition as claimed in claim 4 in which $R_1$ represents 2-ethylhexyl.

8. A composition as claimed in either of claims 2 or 3 in which the viscosity of the tacky copolymer is less than 50,000 cp at 350° F. and the vinyl lactam is present in the form of poly(vinyl pyrrolidone) in an amount from 1 to 8% by weight of the blend.

* * * * *